United States Patent [19]
Light et al.

[11] Patent Number: 5,514,181
[45] Date of Patent: May 7, 1996

[54] ABSORBABLE STRUCTURES FOR LIGAMENT AND TENDON REPAIR

[75] Inventors: Nicholas D. Light, Doune; James MacGregor, Glasgow; Wilson Harvey, Gargunnock; Paul W. Watt, Broomridge, all of United Kingdom

[73] Assignee: Johnson & Johnson Medical, Inc., Arlington, Tex.

[21] Appl. No.: 314,986

[22] Filed: Sep. 29, 1994

[30] Foreign Application Priority Data

Sep. 29, 1993 [GB] United Kingdom ............... 9320100

[51] Int. Cl.$^6$ ............................................. A61F 2/08
[52] U.S. Cl. ............................... 623/13; 623/12; 606/229
[58] Field of Search ............................ 623/13, 11, 12; 606/229, 230, 154

[56] References Cited

U.S. PATENT DOCUMENTS

| | | | |
|---|---|---|---|
| 3,366,440 | 1/1968 | Nuwayser | 606/229 |
| 3,797,047 | 3/1974 | Pillet | 623/13 |
| 4,127,902 | 12/1978 | Homsy | 623/13 |
| 4,320,201 | 3/1982 | Berg et al. | |
| 4,614,794 | 9/1986 | Easton et al. | |
| 4,787,900 | 11/1988 | Yannas | 623/1 |
| 4,942,875 | 7/1990 | Hlavacek et al. | 606/230 |
| 5,171,273 | 12/1992 | Silver et al. | |
| 5,263,983 | 11/1993 | Yoshizato | 623/12 |
| 5,263,984 | 11/1993 | Li et al. | 623/13 |

FOREIGN PATENT DOCUMENTS

| | | |
|---|---|---|
| 2092344 | 9/1993 | Canada . |
| WO85/00511 | 2/1985 | European Pat. Off. . |
| 274898 | 7/1988 | European Pat. Off. . |
| WO88/06872 | 9/1988 | European Pat. Off. . |
| 0194192A1 | 9/1986 | France . |
| 0241252A2 | 10/1987 | United Kingdom . |
| WO90/00060 | 1/1990 | WIPO . |
| 9203988 | 3/1992 | WIPO .................... 623/13 |
| 9409720 | 5/1994 | WIPO .................... 623/13 |

*Primary Examiner*—David H. Willse
*Assistant Examiner*—Bruce E. Snow
*Attorney, Agent, or Firm*—Andrew C. Farmer

[57] ABSTRACT

A fully absorbable prosthesis (1) for the repair of damaged ligaments and/or tendons in the form of a multilayer spiral roll comprising the following spiral layers: a foraminous layer (2) of a synthetic bioabsorbable material; a bioabsorbable film (3); and a layer (4) of a bioabsorbable biopolymer sponge. The invention also provides a method of making such a prosthesis, comprising the steps of: providing a laminate of a foraminous layer of bioabsorbable material and a bioabsorbable film; coating the laminate with a layer of an aqueous gel comprising a bioabsorbable polymer; rolling up the laminate and the gel layer into a spiral roll, followed by drying the gel to form a layer of bioabsorbable sponge. The foraminous layer (2) preferably comprises a synthetic bioabsorbable polymer having high tensile strength. The bioabsorbable film (3) and sponge layer (4) preferably comprise a chemotactic biopolymer such as collagen.

15 Claims, 3 Drawing Sheets

ABSORBABLE STRUCTURES FOR LIGAMENT AND TENDON REPAIR

The present invention relates to absorbable structures for use as temporary prostheses in the repair of damaged ligaments and/or tendons.

Damage to ligaments and/or tendons is a frequent occurrence, particularly as a consequence of violent exercise or contact sports. An especially common and difficult to treat sports injury is tearing of the anterior cruciate ligament (ACL) of the knee.

Various approaches have been tried to restore the function of torn tendons or ligaments. The simplest approach is simply to suture together the torn ends of the ligament or tendon. However, the healing rate of ligaments or tendons sutured in this way is extremely slow, and even after healing is complete the strength of the ligament or tendon is substantially reduced. Moreover, the scar tissue tends to propagate into surrounding tissues causing discomfort and loss of mobility.

In another approach, the ligament or tendon is replaced by a permanent prosthesis of biocompatible but non-resorbable material, such as Dacron®, PTFE or polypropylene. A favoured permanent prosthesis consists of bundles of carbon fibers, optionally coated with a biocompatible polymer. However, none of the permanent prostheses has proved to be sufficiently durable to replace a ligament or tendon for the life of a user. In particular, it has been found that the carbon-fiber based prostheses tend to crack after 12–18 months of use, thereby releasing carbon particles that can cause severe inflammatory reactions and even arthritis.

A further approach to the repair of damaged tendons or ligaments has been to implant a temporary, biodegradable prosthesis that can stabilize the tendon or ligament and provide a framework for healing of the tendon or ligament while gradually being absorbed into the body. Accordingly, the requirements for such a temporary prosthesis include: high tensile strength to restore tendon or ligament function, slow but complete bioabsorption in situ, low antigenicity, and a directional (uniaxial) structure that promotes formation of strong, well-oriented scar tissue by directional ingrowth of fibroblasts from the undamaged ends of the ligament or tendon.

WO85/00511 describes a collagen-based material for regeneration of ligaments and/or tendons. The material is formed from strands of collagen that have been cross-linked with glutaraldehyde to increase their tensile strength. The collagen strands are provided in the form of a suitable weave with sufficient space between the strands to function as a "scaffold" through which ligament fibroblasts can propagate. A sheet of the collagen weave may be rolled up to form a cylinder of spiral cross-section which positioned between ends of e.g. a torn anterior crucia ligament, the ends of the cylinder being sutured to the undamaged ends of the ligament. The joint is immobilized, and healing of the ligament is said to be completed in as little as three weeks.

Similarly, U.S. Pat. No. 5,171,273 describes absorbable ligament or tendon prostheses formed from high-strength collagen fibers. The high-strength collagen fibers are formed by the steps of: dissolving type I collagen in dilute HCl, extruding the solution into a special buffer bath to reconstitute the collagen fibers, and cross-linking the reconstituted fibers using glutaraldehyde or a combination of severe dehydration and treatment with cyanamide. The fibers are woven, twisted or braided together to form the absorbable ligament and/or tendon prostheses.

A drawback of tendon and/or ligament prostheses that are formed solely from collagen is that the collagen loses its tensile strength rapidly in vivo, even when cross-linked as described above. This characteristic of collagen is incompatible with the relatively long healing times required for repair of ligaments or tendons.

WO88/06872 describes an implantable prosthesis for the repair of tendons or ligaments, characterized by a structure of a bioabsorbable material other than proteins or polypeptides or derivatives thereof. The structure exhibits longitudinal grooves or channels intended to serve as initial propagation guides for new fibrous tissue. For example, the prosthesis may consist of a plurality of concentric tubes of a synthetic bioabsorbable polymer, such as a copolymer of lactic and glycolic acids, polyhydroxy butyric acid or the like. The interstices between the tubes provide the longitudinal channels for tissue ingrowth.

EP-A-0241252 describes an absorbable ligament or tendon prosthesis formed from melt-spun filaments of a special end-capped lactide polymer having exceptionally high tensile strength. The filaments are plied, twisted or braided to form the ligament or tendon prosthesis. The twist or braid provides a relatively open structure which is geometrically capable of allowing natural tissue to be deposited along the filaments and develop natural tendon or ligamentous tissue.

A drawback of the above absorbable prostheses based solely on synthetic, non-collagenous polymers is that the prostheses cannot exhibit the beneficial wound-healing properties of biopolymers such as collagen. It is well known that wound-healing cells such as fibroblasts have a special affinity for collagen and certain other biopolymers. This property is termed the chemotactic effect of collagen.

A further drawback of all previous absorbable tendon and/or ligament prostheses is that the porosity of the prostheses to cellular invasion by fibroblasts is not optimised. It has been determined that a pore or channel size in the range 50–250 μm is preferred for promoting cellular invasion, but hitherto the implant materials have not provided a controlled porosity in this range.

Accordingly, it is an object of the present invention to provide fully bioabsorbable ligament and/or tendon prostheses that combine high tensile strength, chemotactic properties and optimised porosity for directional cellular invasion and healing.

The present invention provides a bioabsorbable ligament or tendon prosthesis in the form of a multilayered spiral roll comprising the following spiral layers: a foraminous layer of a synthetic bioabsorbable material; a bioabsorbable film, and a layer of a bioabsorbable sponge.

The prostheses according to the present invention are in the form of a multilayered spiral roll, also known as a "Swiss roll" structure. That is to say, the prostheses are formed by rolling up a plurality of overlapping layers into a cylindrical roll. Each of the layers is thereby rolled into a spiral roll that is coaxial with and radially alternating with the other layers.

The spiral roll preferably has a diameter in the range of from 1.2 to 21 mm, more preferably 3.0 to 10.0 mm. The length of the spiral roll is preferably 5 to 80 mm. The spiral roll preferably contains from 2 to 6 complete 360° turns of the spiral.

The chief function of the foraminous layer of a synthetic bioabsorbable material is to provide tensile strength to the prosthesis. The foraminous nature of this layer enhances the flexibility of the prosthesis and allows easy suturing of the prosthesis. Preferably the foraminous layer is a woven, non-woven or knitted mesh.

Preferably, the foraminous layer comprises a polymer or copolymer of lactic acid or glycolic acid, oxidized regenerated cellulose, polydioxanone (PDS), a copolymer of lactic acid and ε-caprolactam, polyhydroxybutyric acid or a copolymer of hydroxybutyric acid and hydroxyvaleric acid. More preferably, the foraminous layer comprises one of the copolymers of lactic acid and glycolic acid sold under the Registered Trade Mark VICRYL, or the oxidized regenerated cellulose sold under the Registered Trade Mark SURGICEL. Most preferably, the foraminous layer comprises the melt-spun polylactide or polylactide/polyglycolide copolymer described in EP-A-0241252.

The foraminous layer does not need to be bonded to either the continuous film or to the sponge layers. However, preferably, the foraminous layer is bonded to one or both of the film or the sponge layer, and more preferably the foraminous layer is actually embedded in one or other of the film or the sponge layer, as described further below.

The maximum thickness of the foraminous layer is preferably in the range 0.02 to 0.3 mm, more preferably 0.04 to 0.1 mm.

The bioabsorbable film is a continuous or substantially continuous layer of bioabsorbable material that serves to block cellular migration in radial directions inside the prosthesis. That is to say, the barrier layer of bioabsorbable film serves to guide cellular migration axially along the prosthesis, resulting in the formation of well oriented and strong replacement tissue. The bioabsorbable film is preferably formed by drying an aqueous solution or suspension comprising a biopolymer such as collagen, a glycosaminoglycan such as hyaluronic acid, or the like. Preferably, the bioabsorbable film contains a bioabsorbable plasticiser. Preferably the plasticiser is a polyhydric alcohol such as glycerol, and preferably it is present in an amount of 5% to 50% w/w.

The biopolymer is preferably cross-linked to reduce the rate at which it is bioabsorbed. Preferred cross-linking agents include aldehydes such as glutaraldehyde, isocyanates and carbodiimides. The biopolymer film preferably also contains oil microdroplets dispersed-therein in order further to reduce the rate of bioabsorption. The oil microdroplets may comprise any biocompatible and bioabsorbable oil, such as sunflower seed oil, sesame seed oil or fish oil. Preferably, the oil is present in an amount of 1 to 90% by weight, more preferably 10 to 75% by weight based on the weight of the biopolymer film.

Preferably, the foraminous layer is actually coated with the bioabsorbable film or embedded therein, so that the interstices in the foraminous layer are substantially all filled by the material of the bioabsorbable film. Particularly preferred composite materials comprising a reinforcing mesh embedded in a collagen film are described and claimed in EP-A-0194192.

The thickness of the bioabsorbable film (except when it forms a composite with the foraminous layer) is preferably in the range 0.01–0.1 mm, and more preferably 0.015–0.03 mm.

The layer of a bioabsorbable biopolymer sponge serves as a spacer between the coils of the reinforcing layer and the bioabsorbable film, defining a uniform and directional interstitial channel for cellular invasion. The porosity of the sponge and the chemotactic effect of the biopolymer combine to promote rapid invasion by fibroblasts, resulting in rapid tissue regeneration. Preferably, the sponge comprises collagen, a glycosaminoglycan such as chondroitin sulfate or hyaluronic acid or a mixture of such biopolymers. Preferably, the porosity of the sponge is optimised for maximum cellular ingrowth, implying that at least 80% of the pores have an average pore diameter in the range 50 μm–250 μm. Such relatively small pore sizes can be obtained, for example, by flash freezing of a collagen solution or suspension (resulting in very small ice crystals) followed by freeze drying, as described in WO90/00060. Alternatively or additionally, small pore sizes may be obtained by including a volatile anti-freeze such as ethanol or isopropanol in the gel, preferably in an amount of 5–25% w/v. The presence of the anti-freeze results in the formation of smaller ice crystals on freezing, and hence smaller pores on freeze-drying.

Preferably, the sponge comprises chemotherapeutic agents in addition to the structural biopolymer. For example, the sponge may contain an antiseptic or an antibiotic. Preferably, the sponge contains a wound healing factor such as a growth factor, a cytokine, an alginate, a glycosaminoglycan or an active derivative thereof. The bioabsorbable film may alternatively or additionally contain the same or a different therapeutic agent or agents.

Preferably, the structural biopolymer of the sponge is cross-linked to reduce the rate of bio-absorption of the sponge. Preferably, the structural biopolymer is collagen and the cross-linking agent is one of those described above for the bioabsorbable film. Also preferably, the biopolymer sponge contains preferably 1 to 90% by weight, more preferably 10 to 75% by weight based on the weight of the sponge, of oil microdroplets dispersed therein. The oil may be any biocompatible and biodegradable oil such as sunflower seed oil, sesame seed oil or fish oil. The presence of the oil microdroplets substantially reduces the rate of bio-absorption of the sponge. Furthermore, the oil microdroplets can be used as vehicles for hydrophobic, oleophilic therapeutic agents.

Preferably, the thickness of the sponge layer is in the range 0.5 to 2.5 mm, more preferably 1.0 to 1.5 mm.

Preferably, the sponge layer has embedded therein one or more solid bioabsorbable rods extending longitudinally through part or all of the prosthesis. The rods may be sections of bioabsorbable stuture, preferably collagen suture. The rods enhance the uniaxial directionality of the sponge layer and reduce the rate at which the layer is absorbed in vivo.

The present invention also provides the use of a bioabsorbable prosthesis as described above for the preparation of a surgical implant for the repair of a damaged tendon or ligament.

The present invention further provides a method of making a bioabsorbable prosthesis for use in surgical repair of a damaged ligament or tendon, the method comprising the steps of: providing a laminate of a foraminous layer of bioabsorbable material and a bioabsorbable film; coating the laminate with a layer of an aqueous gel comprising a bioabsorbable polymer; rolling up the laminate and the gel layer into a spiral roll, followed by drying the gel to form a layer of bioabsorbable sponge.

Preferably, the gel is dried to form the bioabsorbable sponge by freezing (preferably flash freezing), followed by freeze-drying by evaporation of water from the gel under reduced pressure. In alternative preferred methods, the gel is frozen or flash-frozen and the frozen gel is then solvent dried by treatment with a hygroscopic solvent such as isopropyl alcohol.

The laminate comprises overlapping layers of the foraminous layer of bioabsorbable material and the bioabsorbable film. Preferably, the laminate comprises a high tensile strength foraminous mesh embedded in a film of a biopolymer such as collagen, as described in EP-A-0194192.

The compositions of the foraminous layer and the bioabsorbable film may be the same or different, and are preferably as defined above for preferred embodiments of the tendon or ligament prostheses of the present invention.

Preferably, the aqueous gel comprises acid-swollen collagen fibers, preferably at a concentration of 0.1%–5% w/v. In preferred methods, fibrous collagen is extracted from bovine corium or tendon and pre-washed to remove the majority of non-collagenous components as described in U.S. Pat. Nos. 4,614,794 or 4,320,201. The collagen is then suspended in clean deionised pyrogen-free water and homogenised to a fine fibrous suspension by passage through a homogenising system. Suitable homogenising systems are described in U.S. Pat. No. 4,320,201.

Homogenization is continued until a desired degree of fiber division is achieved. This results in a preferred fiber size in the range 0.01 to 10 mm.

The homogenized collagen is acidified to cause it to swell and form a gel suitable for freeze drying. The acidifying step may use an organic acid such as formic, acetic, propionic, lactic or malonic, or dilute inorganic acids such as hydrochloric acid. Preferably the homogenized collagen suspension is acidified to pH 2 to 6, more preferably pH 3.0 to 4.5.

Chemotherapeutic agents, preferably as described above, may be dispersed in the aqueous gel of the bioabsorbable polymer, preferably in an amount of 0.1% to 50% w/w, based on the dry weight of the sponge. Also preferably, microdroplets of a bioabsorbable oil may be dispersed in the aqueous gel by emulsification at high shear (collagen is an effective emulsifier). Preferably, the oil microdroplets are present in an amount of from 1% to 90% by weight, more preferably 10% to 75%, based on the dry weight of the sponge.

Preferably, the aqueous gel is dried by flash freezing at temperatures below −20° C., followed by freeze drying, preferably as described in WO90/00060. The flash freezing results in smaller ice crystals, and thus provides smaller pores in the freeze-dried sponge. The pore size of the freeze-dried sponge may also be reduced by adding volatile anti-freeze substances such as ethanol or isopropanol to the aqueous gel before it is frozen, since these also will tend to reduce the size of the ice crystals formed on freezing. Preferably, the anti-freeze substance is added in an amount of 5%–25% w/v, based on the volume of the gel.

Preferably, the freeze-drying step is carried out either by evaporating the water (and other volatile components) from the frozen gel under reduced pressure, or by solvent drying, which involves treating the frozen gel with a hygroscopic solvent, such as isopropyl alcohol, to extract the water from the frozen gel. Surprisingly, it has been found that the presence of volatile antifreeze agents such as ethanol or isopropyl alcohol in the frozen gel results in accelerated solvent drying.

Preferably, the laminate with the layer of aqueous gel thereon is rolled up through 2 to 6 complete 360° revolutions prior to drying. The aqueous gel may be prechilled to 0°–5° C. prior to the rolling-up step in order to increase the rigidity of the gel and reduce the gel lost by squeezing out of the ends of the roll. Preferably, the rolling-up step is initiated by rolling up about a small diameter bobbin, e.g. a hypodermic needle, which is removed after the rolling up is complete. A small excess of the aqueous gel (up to 50% excess) may be used to compensate for gel lost in the rolling-up step.

In other preferred methods according to the invention, one or more bioabsorbable rods is laid atop the laminate and extending substantially parallel to the axis about which the laminate is to be rolled up. The bioabsorbable rods are preferably sections of bioabsorbable suture, and preferably comprise collagen. The rods help to ensure a uniform thickness for the sponge layer in the dried prosthesis.

In yet other preferred embodiments, the method according to the present invention may further comprise the step of incubating the dried prosthesis in vitro with host cells such as host synovial cells or host fibroblast cells prior to implantation. The cells may even be injected into the body of the prosthesis. After a suitable time to achieve required cellular growth and proliferation in the prosthesis, the structure can be implanted in the body.

A specific embodiment of the tendon or ligament prosthesis of the invention will now be described further, by way of example with reference to the accompanying drawings, in which.

Figure 1:
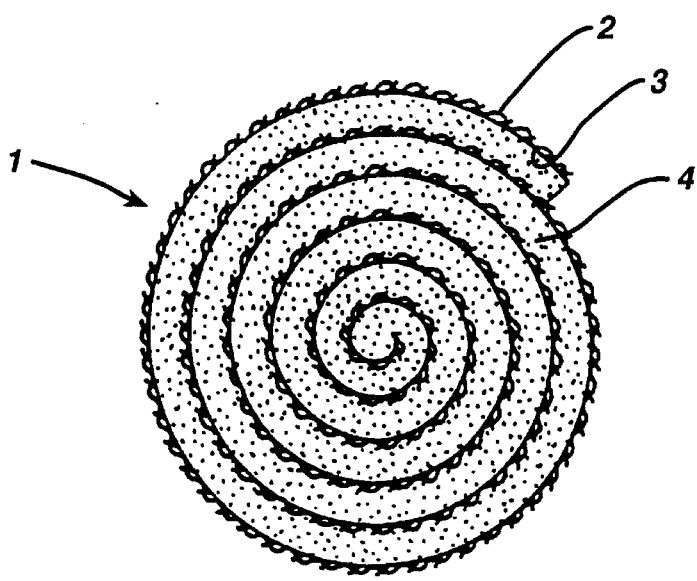
FIG. 1 illustrates a transverse cross-section through a bioabsorbable prosthesis according to the present invention.

Referring to FIG. 1, the prosthesis 1 comprises a multilayered laminate 10 rolled into a spiral shape and consisting of a foraminous layer 2 of a synthetic bioabsorbable material, a bioabsorbable film layer 3 and a layer 4 of bioabsorbable sponge. The foraminous layer 2 is composed of a polylactide/polyglycolide mesh sold under the Registered Trade Mark VICRYL. The bioabsorbable film 3 is composed of Type I collagen fibers cross-linked with hexamethylene diisocyanate. The sponge layer 4 is also formed from Type I collagen fibers cross-linked with hexamethylene diisocyanate.

Figure 4:
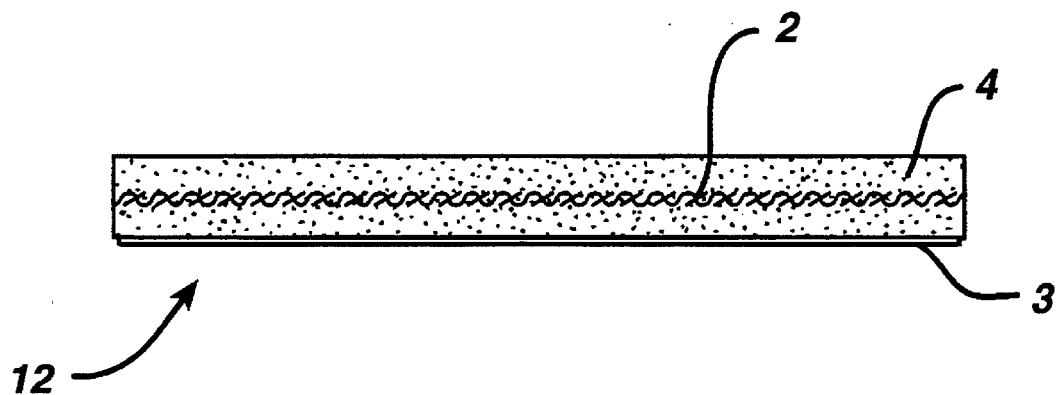
FIG. 4 illustrates an alternate laminate structure for forming a bioabsorbable prosthesis according to the present invention.
Figure 5:
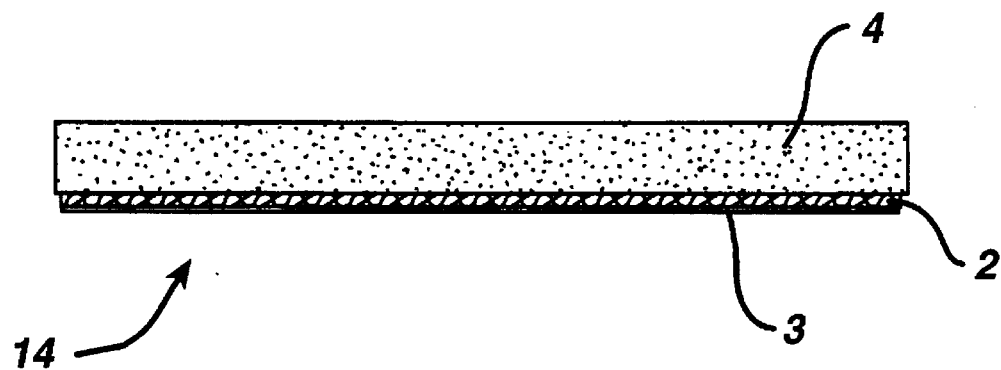
FIG. 5 illustrates a further alternate laminate structure for forming a bioabsorbable prosthesis according to the present invention.

FIG. 4 illustrates an alternative structure of laminate 12 wherein the foraminous layer 2 is embedded within the sponge layer 4. FIG. 5 illustrates an alternative structure of laminate 14 wherein the foraminous layer 2 is embedded within the film layer 3.

Figure 3:
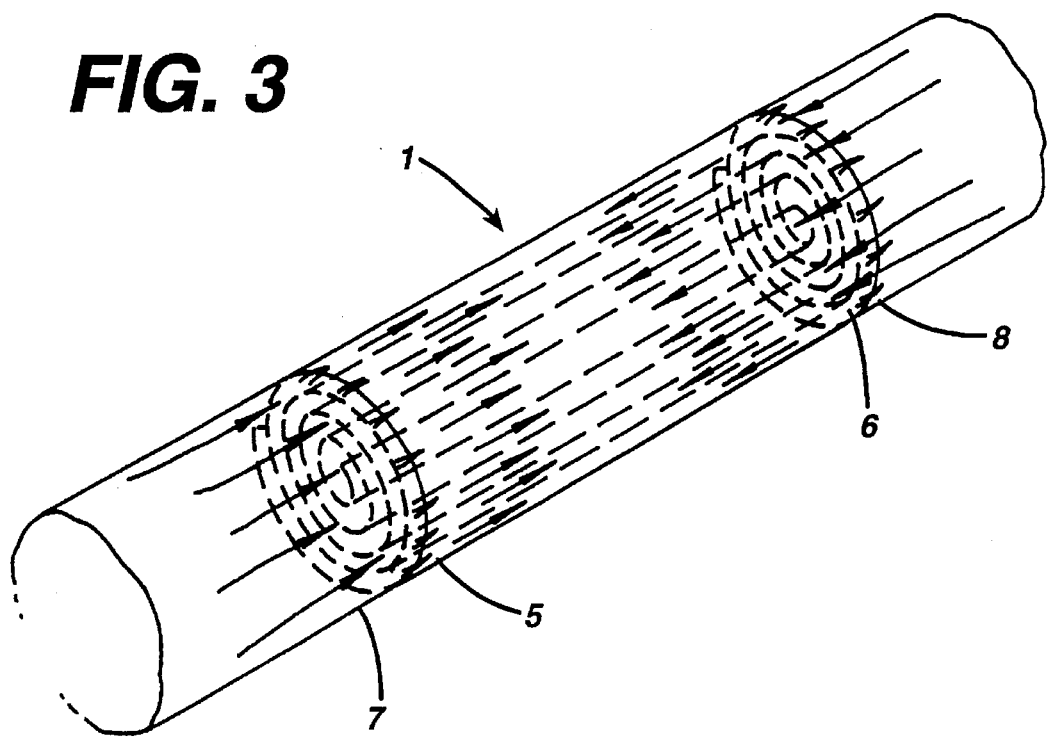
FIG. 3 illustrates the bioabsorbable prosthesis of FIG. 1 in use to repair a severed ligament.
Figure 2:
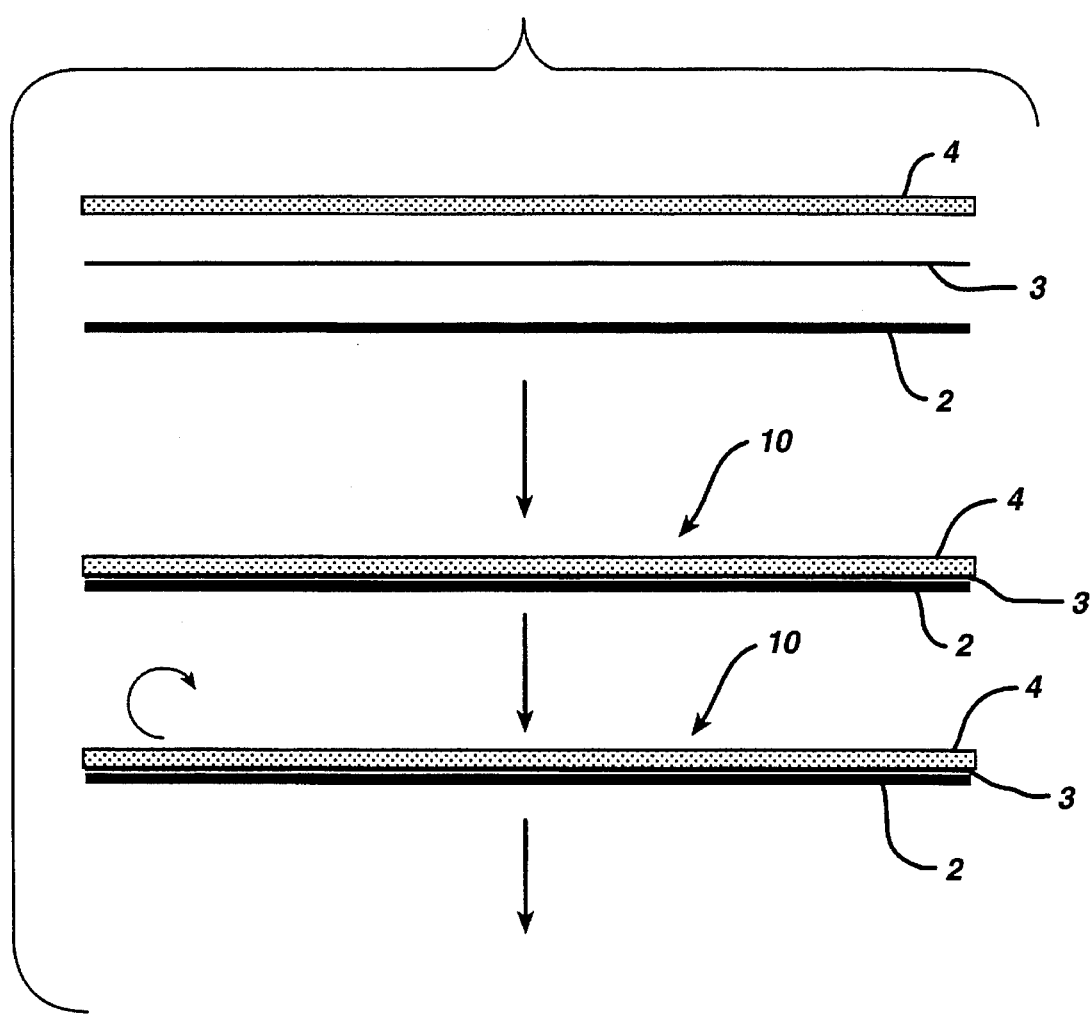
FIG. 2 illustrates stages in the method of making the bioabsorbable prosthesis of FIG. 1.

In use, the prosthesis 1 is used to replace part or all of a damaged ligament or tendon, as shown in FIG. 3. The ends 5, 6 of the prosthesis are sutured to the undamaged ends 7, 8 of the ligament or tendon. Alternatively, one of the ends 5, 6 of the prosthesis may be attached directly onto a bone or into a socket provided in a bone.

FIG. 3 also shows schematically, by means of arrows, the direction of cellular migration and tissue ingrowth into the prosthesis 1 from the undamaged ends 7, 8 of the ligament or tendon. The cells, especially fibroblasts, migrate rapidly into the collagen sponge on account of its porosity and the chemotactic effect of collagen. However, the cell migration is highly directional, since the collagen sponge spiral layer 4 defines a longitudinal channel for cellular migration. Radial cellular migration is blocked by the bioabsorbable film layer 3. The VICRYL mesh layer 2 provides the necessary tensile strength to the prosthesis while retaining sutureability.

Specific embodiments of method of manufacture of prosthesis according to the present invention will now be described further, by way of the following examples:

EXAMPLE 1

A prosthesis for a ligament or tendon according to the present invention comprising separate layers of foraminous synthetic bioabsorbable polymer, bioabsorbable film, and bioabsorbable sponge is prepared as follows:

A. Preparation of Collagen Slurry

Fibrous collagen, obtained from bovine corium and pre-washed to remove the majority of non-collagenous components as described in U.S. Pat. Nos. 4,614,794 or 4,320,201 is suspended in clean deionised pyrogen-free water at 0.45% w/v concentration and homogenised to a fine fibrous suspension by passage through a homogenizing system similar to that described in U.S. Pat. No. 4,320,201. Homogenisation is continued until the collagen fiber size is in the range 0.1–1.0 mm. The suspension is acidified to pH 4.5 with acetic acid to swell the collagen.

B. Preparation of Collagen Film Layer

To the collagen gel prepared in Step A above glycerol is added as a plasticiser to a final weight of 0.5% w/w and the gel is then spread in a flat tray having a non-stick surface (e.g. PTFE) to a depth of about 2 mm. The gel is then dried in warm air to leave a continuous, flexible film of collagen about 0.02 mm thick.

C. Preparation of Laminate

A piece of VICRYL® polylactide/polyglycolide mesh of rectangular shape and dimensions approximately 20 mm×40 mm× 0.1 mm is placed in a flat-bottomed tray. A piece of the collagen film prepared in Step B of identical size and shape is placed atop the VICRYL mesh.

D. Preparation of the Prosthesis

A layer of the collagen gel prepared as in Step A but containing 0.5% w/v collagen solids and 10% w/v isopropanol, and with a final pH of 4.5 is spread approximately 1–2 mm deep across the top surface of the laminate prepared in Step C. The gel is quickly degassed and the laminate with the gel layer thereon is quickly but gently rolled up around one long edge of the rectangular piece. The resulting helical coil is flash frozen as described in WO90/00060 followed by freeze drying to produce the prosthesis. In the resulting collagen sponge layer, at least 80% of the pores have average pore sizes in the range 35 to 250 µm, which is near-optimum for cellular invasion.

EXAMPLE 2

A prosthesis for the repair of a ligament or tendon according to the present invention, in which the foraminous synthetic bioabsorbable layer is embedded in the bioabsorbable film is prepared as follows:

First, a collagen slurry is prepared as in Step A of Example 1, and a glycerol plasticiser is added to the slurry as in Step B. A layer of VICRYL mesh is placed in the bottom of a flat tray having a non-stick (e.g. PTFE) surface, and the slurry is then poured over the VICRYL mesh to a depth of about 2 mm, thereby immersing the VICRYL mesh in the collagen slurry. The slurry is then dried in warm air to produce a composite layer of material comprising the VICRYL mesh embedded in a collagen film. The preparation of such composite layers is described in detail in EP-A-0194192.

A rectangular piece of the composite material of dimensions 20 mm×40 mm is then used as the laminate in Step D above to produce the desired prosthesis.

EXAMPLE 3

A bioabsorbable prosthesis for the repair of a ligament or tendon having oil microdroplets dispersed in the bioabsorbable film and in the bioabsorbable sponge is prepared as follows:

A collagen slurry is prepared as in step A of Example 1. To this slurry is added sesame seed oil at 50% (as % of the collagen content w/w), and the mixture is homogenized at high shear to emulsify the sesame seed oil. The collagen serves as an effective emulsifier. The remaining steps of the method are carried out as described above for Example 2.

The resulting prosthesis undergoes substantially slower bioabsorption and loss of tensile strength in vivo than the prosthesis produced in Example 2.

The above specific embodiment and examples are intended for the purpose of illustration only. Many other embodiments and methods according to the present invention as defined in the accompanying claims will be apparent to the skilled reader.

We claim:

1. An axially elongated bioabsorbable ligament or tendon prosthesis in the form of a multilayered spiral roll comprising:

a laminate comprising:
a foraminous layer of a synthetic bioabsorbable material;
a layer of bioabsorbable film;
a layer of a bioabsorbable sponge; and
wherein the laminate is spirally wound about itself such that multiple layers of the laminate overlap radially and form the axially elongated prosthesis and whereby the foraminous layer provides strength to the prosthesis, the layer of bioabsorbable sponge promotes cellular ingrowth into the prosthesis and the layer of bioabsorbable film radially limits cellular ingrowth into the prosthesis.

2. A bioabsorbable prosthesis according to claim 1, wherein the diameter of the multilayered spiral roll is from 1.2 to 21 mm.

3. A bioabsorbable prosthesis according to claim 1, wherein the foraminous layer comprises a polymer or copolymer of lactic acid and/or glycolic acid, oxidised regenerated cellulose, polydioxanone (PDS), a copolymer of lactic acid and ϵ-caprolactam, polyhydroxybutyric acid or a copolymer of hydroxybutyric acid and hydroxyvaleric acid.

4. A bioabsorbable prosthesis according to claim 1, wherein the foraminous layer is embedded in the bioabsorbable film or in the sponge layer.

5. A bioabsorbable prosthesis according to claim 1 wherein the maximum thickness of the foraminous layer is in the range 0.02 to 0.3 mm.

6. A bioabsorbable prosthesis according to claim 1, wherein the bioabsorbable film comprises a biopolymer or a chemically cross-linked biopolymer derivative.

7. A bioabsorbable prosthesis according to claim 6, wherein the biopolymer comprises collagen or a glycosaminoglycan.

8. A bioabsorbable prosthesis according to claim 1, wherein oil microdroplets are dispersed in the bioabsorbable film.

9. A bioabsorbable prosthesis according to claim 8, wherein the oil is present in an amount of from 1% to 90% by weight, based on the weight of the bioabsorbable film.

10. A bioabsorbable prosthesis according to claim 1, wherein the thickness of the bioabsorbable film is in the range 0.01 to 0.1 mm.

11. A bioabsorbable prosthesis according to claim 1, wherein the bioabsorbable sponge comprises a biopolymer or a chemically cross-linked biopolymer derivative.

12. A bioabsorbable prosthesis according to claim 11, wherein the bioabsorbable sponge comprises collagen or a glycosaminoglycan.

13. A bioabsorbable prosthesis according to claim 1, further comprising microdroplets of a bioabsorbable oil dispersed in the bioabsorbable sponge.

14. A bioabsorbable prosthesis according to claim 13, wherein the bioabsorbable oil which is present in the amount of from 1% to 90% by weight, based on the weight of the bioabsorbable sponge.

15. A bioabsorbable prosthesis according to claim 1, wherein the thickness of the bioabsorbable sponge layer is in the range 0.5 to 2.5 mm.

* * * * *